United States Patent
Leisieur nee Boivin et al.

(10) Patent No.: US 9,895,298 B2
(45) Date of Patent: Feb. 20, 2018

(54) METHOD FOR EXTEMPORANEOUS AND REVERSIBLE CONCENTRATION OF LIPOSOMES

(75) Inventors: Sylviane Leisieur nee Boivin, Sceaux (FR); Valerie Bernat, Chatenay Malabry (FR); Genevieve Le Bas, Paris (FR); Catherine Ringard nee Lefebvre, Rueil Malmaison (FR)

(73) Assignee: CENTRE NATIONAL DE LA RECHERCHE SCIENTIFIQUE (C.N.R.S.), Paris (FR)

( * ) Notice: Subject to any disclaimer, the term of this patent is extended or adjusted under 35 U.S.C. 154(b) by 1691 days.

(21) Appl. No.: 12/299,261

(22) PCT Filed: Apr. 30, 2007

(86) PCT No.: PCT/FR2007/000742
§ 371 (c)(1),
(2), (4) Date: Jun. 2, 2009

(87) PCT Pub. No.: WO2007/125217
PCT Pub. Date: Nov. 8, 2007

(65) Prior Publication Data
US 2009/0285867 A1 Nov. 19, 2009

(30) Foreign Application Priority Data
May 3, 2006 (FR) .................................. 06 03945

(51) Int. Cl.
| | |
|---|---|
| *A61K 9/127* | (2006.01) |
| *A61K 8/14* | (2006.01) |
| *A61K 8/73* | (2006.01) |
| *A61K 47/40* | (2006.01) |
| *A61Q 19/00* | (2006.01) |

(52) U.S. Cl.
CPC ................. *A61K 8/14* (2013.01); *A61K 8/73* (2013.01); *A61K 9/127* (2013.01); *A61K 47/40* (2013.01); *A61Q 19/00* (2013.01)

(58) Field of Classification Search
CPC ....................................................... A61K 9/127
USPC ........................................... 424/450; 514/58
See application file for complete search history.

(56) References Cited

U.S. PATENT DOCUMENTS

| | | | |
|---|---|---|---|
| 2002/0041895 A1* | 4/2002 | Gregoriadis et al. | 424/450 |
| 2005/0069533 A1* | 3/2005 | Millan et al. | 424/94.64 |
| 2005/0180924 A1* | 8/2005 | Clarot et al. | 424/45 |
| 2005/0208120 A1* | 9/2005 | Albani | 424/450 |
| 2005/0239747 A1* | 10/2005 | Yang et al. | 514/58 |

(Continued)

FOREIGN PATENT DOCUMENTS

| | | |
|---|---|---|
| JP | H02503558 A | 10/1990 |
| JP | 04021627 A | 1/1992 |

(Continued)

OTHER PUBLICATIONS

Nishijo et al in Chemical and Pharmaceutical Bulletin, Pharmaceutical Society of Japan, Tokyo,, JP; vol. 46, No. 1, Jan. 1998, pp. 120-124.*

*Primary Examiner* — Gollamudi Kishore
(74) *Attorney, Agent, or Firm* — Young & Thompson

(57) ABSTRACT

The invention concerns a method for extemporaneous and reversible concentration of liposomes, the mixed liposome-cyclodextrin aggregates obtainable by the method, and uses thereof in the pharmaceutical, diagnostic and cosmetic field.

18 Claims, 11 Drawing Sheets

(56) References Cited

U.S. PATENT DOCUMENTS

Figure 1:
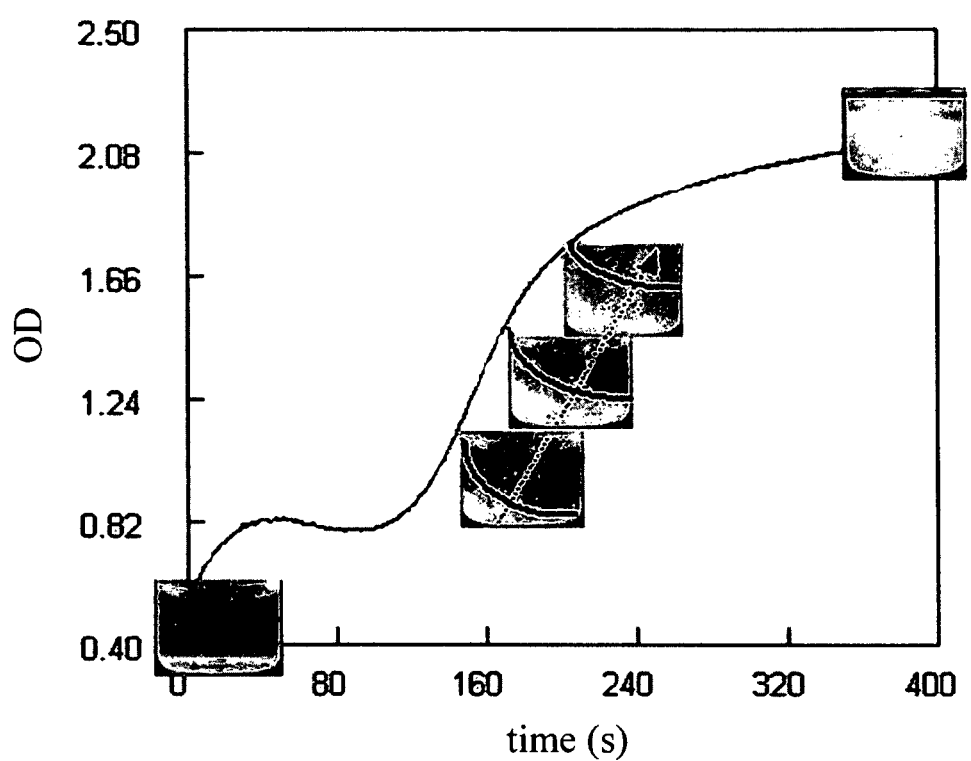

| | | | |
|---|---|---|---|
| 2006/0222694 A1* | 10/2006 | Oh et al. | 424/450 |
| 2007/0026058 A1* | 2/2007 | Pereswetoff-Morath et al. | 424/450 |
| 2007/0065473 A1* | 3/2007 | Miller | 424/401 |

FOREIGN PATENT DOCUMENTS

| | | |
|---|---|---|
| JP | H11512099 A | 10/1999 |
| JP | 2002284798 A | 10/2002 |
| WO | 8809168 A1 | 12/1988 |
| WO | 9707784 A2 | 3/1997 |

* cited by examiner

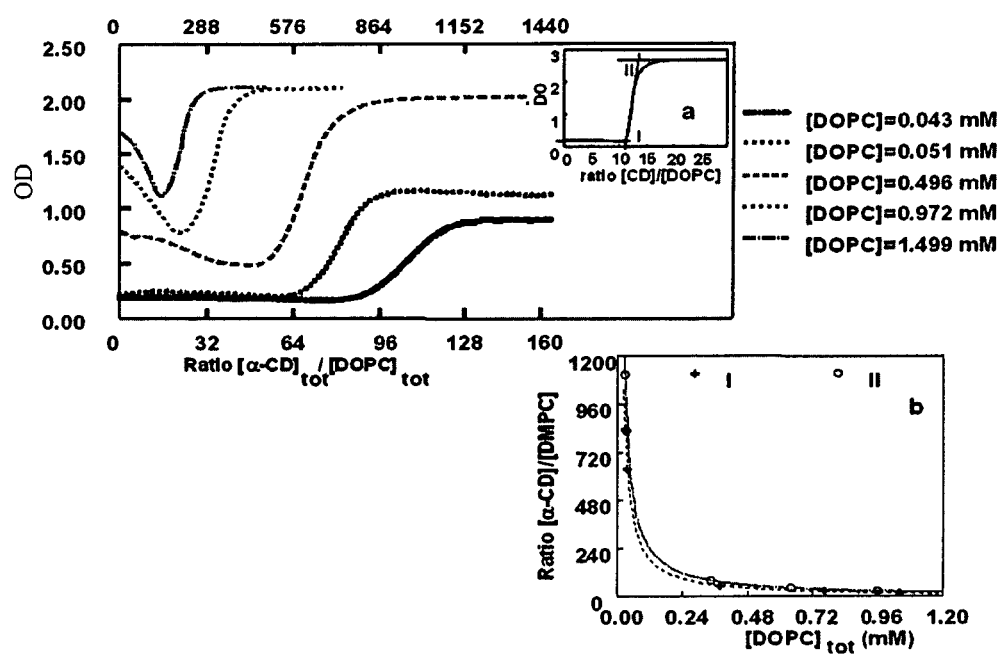
Fig. 3 (a, b)

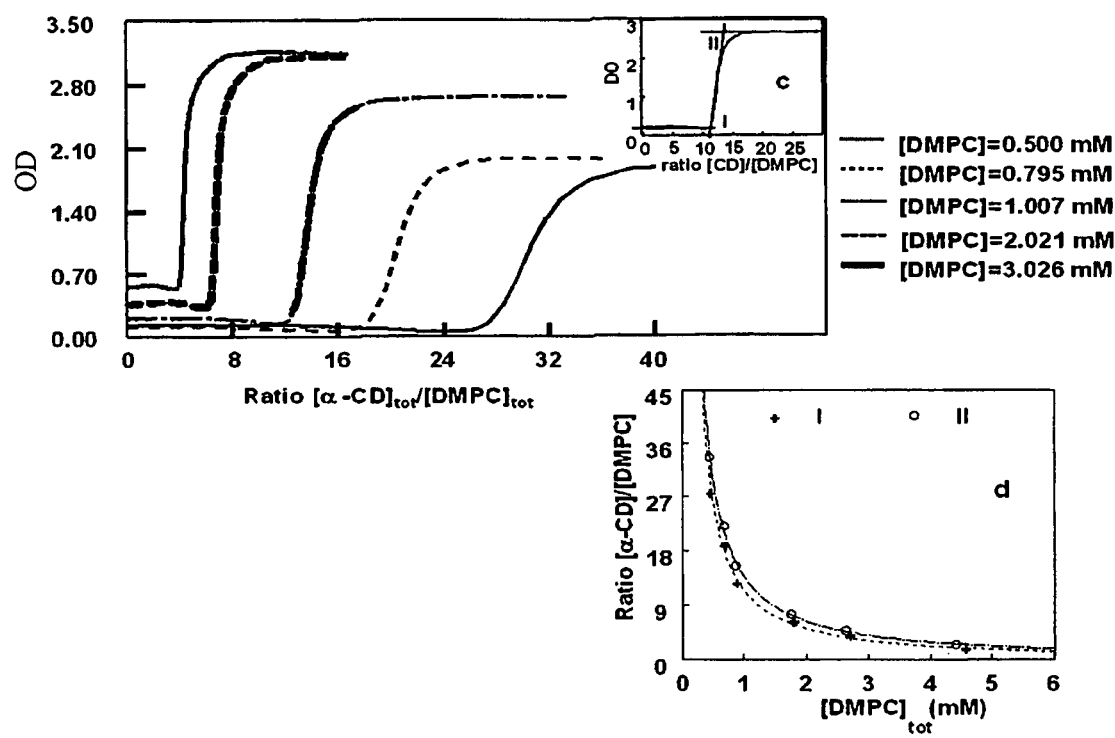
Fig. 3 (c,d)

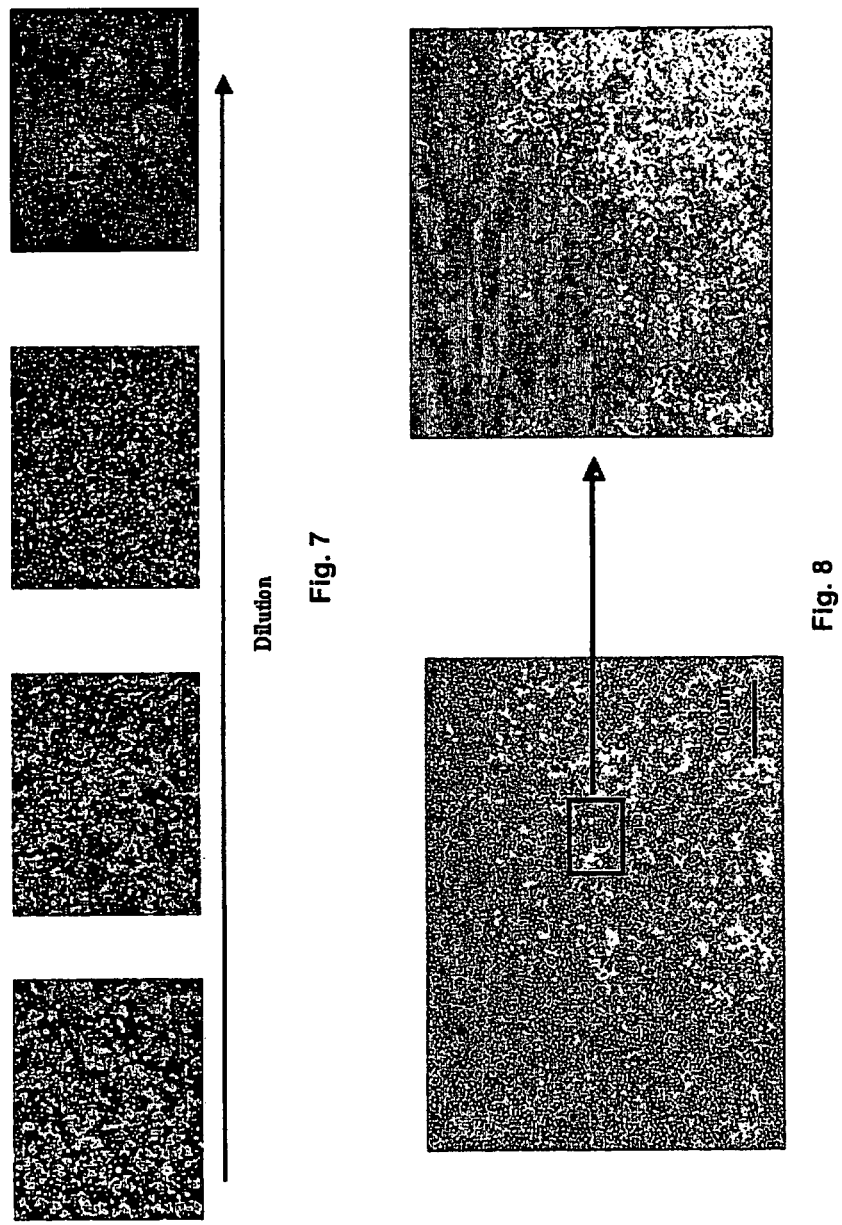

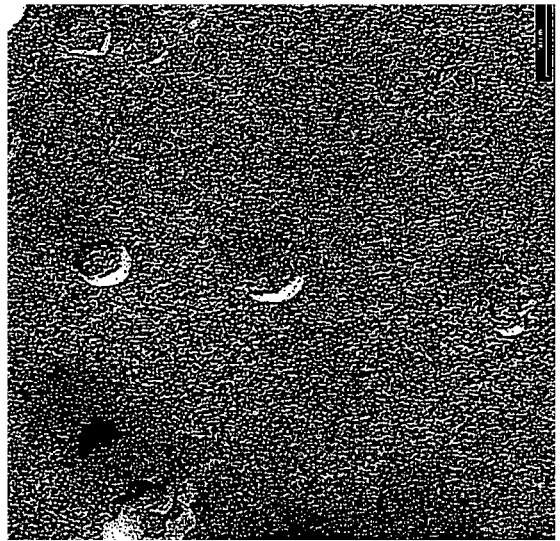
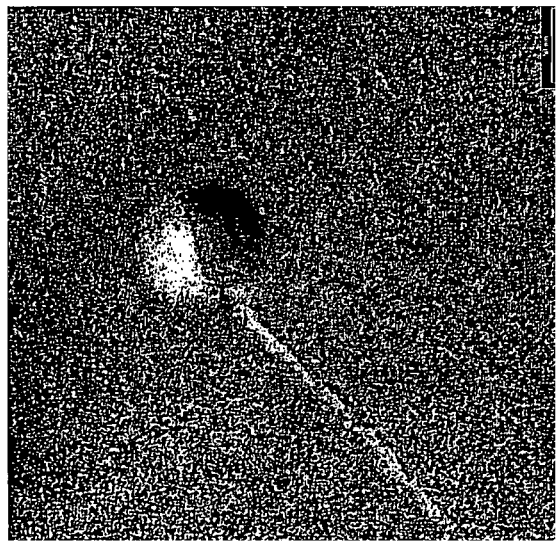
Fig. 11

METHOD FOR EXTEMPORANEOUS AND REVERSIBLE CONCENTRATION OF LIPOSOMES

The present invention relates to a method for extemporaneously and reversibly concentrating liposomes, the mixed liposome-cyclodextrin aggregates which are obtainable by this method, and the uses thereof in the pharmaceutical, diagnostic or cosmetic fields.

Liposomes are vesicles (a few tens of nanometers to several microns in size) which are delimited by one or more bilayers of (phospho)lipids enclosing an aqueous volume. These structures therefore result from the arrangement of amphiphilic molecules which are generally dispersed in a large excess of a continuous aqueous phase. The hydrophilic parts or polar heads of the (phospho)lipids are located on both sides of the bimolecular layers, which form the bilayers and are always in contact with the continuous aqueous medium, whereas the chains of said (phospho)lipids form the core of the membranes, thus minimising the contact thereof with water. This specific structure, composed of aqueous compartments separated by relatively hydrophobic membranes, provides liposomes with the fundamental property, in addition to biocompatibility, of being able to receive and transport hydrosoluble or lipophilic compounds. In the pharmaceutical and cosmetic fields, liposomes, whether they be formed from natural or synthetic lipids, therefore represent potential agents for vectorising active ingredients towards the target tissue. On a more general level, liposomes are nano- or microreservoirs which are able to contain and convey all sorts of products. The actual and potential applications thereof relate equally to a wide range of sectors from fundamental biology to the agro or food chemical industries (cellular model, gene transfer, chemical or enzyme reactors, pesticide formulation, etc.).

The current methods of concentrating liposomes, such as ultracentrifugation or ultrafiltration are laborious to implement, expensive and difficult to transfer to an industrial scale. Moreover, any liposome flocculation or sedimentation process, whether it be spontaneous or caused by the addition of an exogenous substance or energy, generally leads to irreversible liposome aggregation and the risk of causing the liposomes to fuse, and this inevitably involves the loss of the individual characteristics of the liposomes (dimensions, composition, modification of content).

Liposomes can also be concentrated by lyophilisation. However, when the lyophilisate is rehydrated, it is generally found that the initial characteristics of the liposomes have been modified.

Cyclodextrins are cyclic oligosaccharides composed of glucopyranose units, which are bound to one another by an alpha (1-4) oside bond and originate from starch. The macrocyclic chiral structure thereof takes the form of a truncated cone which delimits a very hydrophobic internal cavity (hydrocarbon backbones of glucose units) whereas the external portion remains hydrophilic (hydroxyl groups of glucose units). There is wide variety of natural or modified cyclodextrins, and these have been the subject of many studies and applications in the fields of fundamental research, the pharmaceutical, cosmetic, agro or food chemical industries. This is due to the ability of cyclodextrins to form inclusion complexes with hydrophobic molecules, thus enabling the molecular dispersion thereof in a solvent (aqueous) medium while protecting them from any possible degradation. Furthermore, these cyclodextrins exhibit excellent properties as compression excipients for solid products, emulsifiers or absorption promoters.

Many particulate systems containing cyclodextrins are known. These include in particular poly(cyanoacrylate) nanospheres formed in the presence of cyclodextrins [anionic polymerisation in emulsion], nanocapsules with oily contents or matrix nanoparticles composed of amphiphilic cyclodextrins [the processes of nanoprecipitation, emulsion-solvent evaporation, elimination of mixed micelle surfactant], ethylcellulose microspheres which encapsulate complexes of cyclodextrins and hydrophobic active ingredients [emulsion-solvent evaporation process], microcapsules [prepared by interfacial crosslinking of beta-cyclodextrin with terephthaloyl chloride], and beads [simple mixture of alpha-cyclodextrin and triglycerides].

Mixed liposome-cyclodextrin systems have also been disclosed. These systems are in the form of liposomes which encapsulate a cyclodextrin-active ingredient complex in their aqueous compartment. These systems are prepared by forming the liposomes in the presence of the cyclodextrin-active ingredient complex. The liposomes are produced in a large excess of water and at no point is it disclosed that concentrated mixed [liposome-cyclodextrin] aggregates are obtained.

A process of concentrating liposomes in an extemporaneous and reversible manner which allows the initial characteristics of liposomes to be retained has now been developed.

More specifically, the inventors have surprisingly found that adding cyclodextrins to liposomes in an aqueous dispersion causes the liposomes to flocculate and be deposited, and a concentration of liposomes in the form of mixed liposome-cyclodextrin aggregates is thus obtained. These mixed aggregates are stable as they are, combine the individual properties of the liposomes and the cyclodextrins, and are further easily lyophilisable.

The lyophilisate may advantageously be hydrated without this affecting the initial structure of the liposomes.

The process according to the invention has a number of other advantages.

In particular, the liposomes may contain host substances without said host substances being lost during the process. Furthermore, the liposomes may be redispersed by simply being diluted (reversible system).

Advantageously, this aggregation and disintegration process does not require the use of organic solvent, a heating step or a high degree of energy consumption. In addition, it does not alter the physicochemical characteristics of the initial substances, and this represents a highly beneficial advance in the field of liposome concentration.

In addition, this liposome concentration process does not require any special equipment, centrifuges for example. No stirring is required. The production process does not involve the use of organic solvents or heating, which is an advantage in terms of safety.

Finally, the materials used are easily obtainable on the market at a reasonable cost. The process can easily be adopted on a large scale.

The invention thus provides very simple and inexpensive means for concentrating and redispersing liposomes which may be used in many sectors of the industry.

Furthermore, the mixed liposome-cyclodextrin aggregates obtained by concentration of the liposomes in the presence of cyclodextrins are generally of a micronic size and may advantageously be implemented in new applications by combining the properties of the liposomes and the cyclodextrins.

According to a first aspect, the invention thus relates to a liposome concentration process comprising a step of forming mixed liposome-cyclodextrin aggregates by bringing liposomes dispersed in an aqueous medium into contact with cyclodextrins.

The term "cyclodextrin" is to be understood as the cyclic oligosaccharide which is formed of an α-1,4 chain of at least six hydrosoluble D-glucopyranose units formed from starch, and has a hydrophobic cavity which is capable of trapping lipophilic molecules. The cyclodextrins within the meaning of the present description include natural cyclodextrins or derivatives thereof, provided that said cyclodextrins are hydrosoluble, do not exhibit any detergent or solubiliser properties and do not interact with the lipids forming the liposomes in a way that could cause the vesicle structure thereof to be lost during implementation of the process.

The natural cyclodextrins are cyclic oligosaccharides obtained by the enzymatic hydrolysis of starch. They comprise α, β and γ cyclodextrins (comprising 6, 7 or 8 glucose units respectively), the α-cyclodextrins being particularly preferred.

In the meaning of the present description, the term "cyclodextrin derivatives" refers to natural cyclodextrins, the native structure of which has been modified by being bound covalently to one or more chemical groups, hydrophilic chemical groups in particular. For example, these cyclodextrin derivatives may be a natural cyclodextrin, of which at least one of the hydroxyl functional groups is substituted by a saccharide group. In the meaning of the present description, the cyclodextrin derivatives also include polymerised cyclodextrins.

All or part of the cyclodextrins which are usable according to the process of the invention may be utilised in the form of inclusion complexes, i.e. they contain a small hydrophobic molecule, referred to hereinafter as the "host molecule". Examples of host molecules include, in particular, molecules which are able to develop spectroscopic properties (such as dyes or pigments), radioelements (such as iodine), therapeutic active ingredients (such as some vitamins or anti-inflammatories).

A "liposome" is to be understood as a vesicle, the wall of which is formed from one or more bilayers of amphiphilic molecules enclosing an internal aqueous cavity, said amphiphilic molecules comprising a polar head and hydrophobic residues which are generally alkyl chains or "hydrophobic tails".

The bilayer(s) preferably comprises (comprise) phospholipids.

In particular, the term "liposome" may refer to a biological cell, a prokaryote or eukaryote cell, an animal or vegetable cell or a reconstituted biological "ghost" membrane.

Examples of phospholipids include phosphatidylcholine (PC) and derivatives thereof: egg phosphatidylcholine (Egg-PC), dimyristoylphosphatidylcholine (DMPC), dipalmitoylphosphatidylcholine (DPPC), dioleoylphosphatidylcholine (DOPC), dilauroylphosphatidylcholine (DLPC), distearoylphosphatidylcholine (DSPC), diarachidoylphosphatidylcholine (DAPC) and dilinoleoylphosphatidylcholine (DLPC).

Other phospholipids including, for example, a glycerol group which is bound to two chains of fatty acids and the polar head of which is different from phosphatidylcholine may also be used according to the process of the invention.

Other amphiphilic molecules may also form part of the composition of the liposome bilayers (cholesterol, lipids with a polar head modified by a hydrophilic group, cationic lipids, fluorescent lipids, etc.). The liposomes are preferably predominantly composed of phospholipids.

It goes without saying that the liposomes according to the present invention do not include amphiphilic molecules which are modified by grafting hydrophilic polymers, such as those described in WO 2005/0300170 which, upon interaction with cyclodextrins, lead to destabilisation of the liposome.

The liposomes may be prepared in accordance with conventional techniques including ultrasound irradiation, phase inversion, extrusion, dialysis, resin absorption or gel filtration of mixed lipid-detergent micelles and the freeze-thaw method. For example, the liposomes may be prepared by hydrating a phospholipid film followed by an extrusion process which is sequenced in order to size the vesicles.

The pH and the ionic strength of the aqueous medium are not critical. The aqueous medium may therefore be pure water or a buffered aqueous medium, at a pH of between 6 and 8 in particular, or an aqueous medium containing a monovalent salt, specifically a monovalent cation and a monovalent anion, such as sodium chloride. Said monovalent salt can be added at a preferred concentration of less than or equal to 150 mM. Examples of buffers which may be used according to the invention include, in particular, a phosphate buffer, a PBS buffer, a Hepes buffer or a Hepes buffer+NaCl. The buffers advantageously extend the stability over time of the concentrated mixed liposome-cyclodextrin aggregates obtained according to the process.

The molar concentration of the liposomes in the aqueous medium is not critical and may vary to a large extent. The molar concentration is preferably greater than 0.05 mM, and more preferably between 0.5 mM and 5 mM.

It should be noted that, in this document, the molar concentration of liposomes refers to the molar concentration of the amphiphilic molecules, such as the phospholipids which form the bilayer(s) of the liposome wall.

The concentration of the cyclodextrins in the aqueous medium is also not critical and may vary between 10 mM and 80 mM, in particular between 20 mM and 40 mM, for dioleoylphosphatidylcholine liposomes in particular.

The ratio of the cyclodextrin/liposome molar concentrations in the aqueous medium is greater than 1, in particular between 2 and 1,500.

In general, it has been found that the higher the cyclodextrin-liposome molar ratio, the faster the liposome aggregation process by means of flocculation and sedimentation. Furthermore, the higher the liposome concentration and/or the cyclodextrin concentration, the faster the sedimentation process.

The cyclodextrins are preferably added to the liposomes which are dispersed in an aqueous medium. This process of addition is preferably controlled by means of the concentration and/or the speed of addition (instant or gradual).

According to an embodiment of the invention, all or part of the liposomes contain an exogenous, hydrophilic or hydrophobic substance. In particular, this may be a cosmetic, therapeutic or diagnostic active ingredient, or flavours, fragrances, nutrients, vitamins or pesticides.

These substances are generally molecules or macromolecules which pass through the liposome bilayer in a very limited manner, or do not pass therethrough at all.

The mixed aggregates which are obtained according to the process may be recovered without being destroyed by using conventional methods such as filtration or centrifuging.

According to a particularly preferred embodiment of the invention, the process further comprises a step of lyophilising the mixed liposome-cyclodextrin aggregates obtained according to the process.

According to another preferred embodiment of the invention, the process further comprises a step of dialysing the mixed liposome-cyclodextrin aggregates obtained according to the invention.

According to another preferred embodiment of the invention, the process further comprises a step of rehydrating the lyophilisate of the mixed liposome-cyclodextrin aggregates following the dialysis step.

According to a variant, all or part of the liposomes are biological cells. For example, the aqueous medium may contain a mixture of liposomes which optionally encapsulate an active ingredient and biological cells. The process according to the invention therefore comprises a step of forming mixed liposome-biological cell-cyclodextrin aggregates.

This variant of the process according to the invention is particularly useful for promoting interactions between the liposomes and the biological cells, in particular the fusion or internalisation thereof, or even interactions between the biological cells. The process thus enables an active ingredient contained in the liposomes to pass to the interior of the biological cell.

According to a second aspect, the invention relates to mixed aggregates of liposomes and cyclodextrins which can be obtained by the process according to the invention.

These mixed aggregates advantageously combine the properties of the cyclodextrins on the one hand and the properties of the liposomes on the other. They may thus encapsulate hydrophobic molecules in the cyclodextrin part and/or hydrophobic or hydrophilic molecules or macromolecules in the liposome part. Moreover they can be advantageously broken down by means of dilution without this affecting the individual properties of the components.

These mixed aggregates may be in the form of particles and are generally of a micrometric size, specifically between 100 nm and 10 µm.

According to a variant, the mixed aggregates which can be obtained according to the process are mixed liposome-biological cell-cyclodextrin aggregates.

According to another aspect, the invention concerns a cyclodextrin-enriched concentrated liposome mixture, in particular in the form a lyophilisate, which can be obtained according to the process of the invention.

According to another aspect, the invention relates to the use of the mixed liposome-cyclodextrin aggregates which can be obtained according to the process of the invention to encapsulate exogenic, hydrophilic or hydrophobic substances in cosmetic, pharmaceutical or diagnostic compositions in particular.

The invention can be used in particular to concentrate liposomes which are intended to be used as transporters or vectors of therapeutic or diagnostic active ingredients in the pharmaceutical or chemical fields. The mixed liposome-cyclodextrin aggregates may be used for a transdermal topical application for example. In fact, combining two or three absorption promoters has been found to have synergistic effects in relation to their own individual effects; phospholipids and α-cyclodextrin are both absorption promoters which may be used in the fields of transdermal systems. The mixed aggregates obtained by the process of the invention may also be used for oral administration or administration by absorption via the mucus membranes.

According to another aspect, the invention further relates to the use of cyclodextrins as precursors for the sedimentation of liposomes in an aqueous medium.

FIGURES

FIG. 1: Example of the change in turbidity of a liposome dispersion as a function of time upon the addition of cyclodextrin. The flocculate was obtained from a mixture of DOPC liposomes (0.49 mM), Hepes buffer (pH=7.4) and an α-CD solution (42.09 mM) at 25° C. The optical density (OD) was measured at 400 nm.

Figure 2:
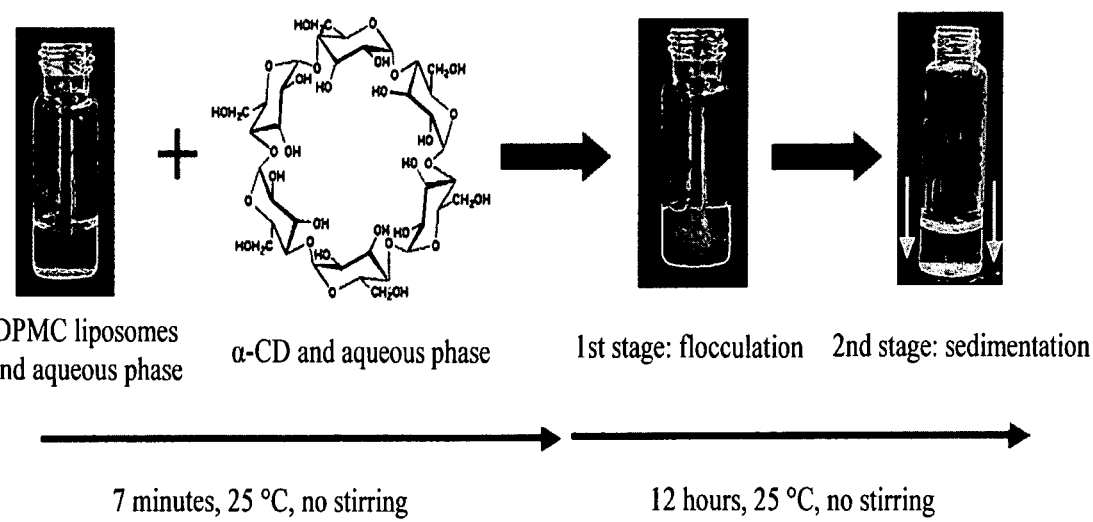

FIG. 2: Stages of liposome concentration after the addition of cyclodextrins. In this case, the system was composed of DOPC liposomes (0.49 mM), Hepes buffer (pH=7.4) and an α-CD solution (42.09 mM).

FIG. 3: Examples of studies of the liposomes concentration process by measuring the turbidity (OD at 400 nm). The curves in Fig. a and c show that the OD increases as a function of the cyclodextrin concentration for different initial liposome concentrations (initial lipid concentrations given in the key) of DOPC (a) and DMPC (c) liposomes. In each curve, the plateau obtained corresponds to the formation of mixed liposome-cyclodextrin aggregates. The curves in figures b and d show the variation in the cyclodextrin/lipid ratio as a function of the lipid concentration in order to achieve flocculation of DOPC (b) and DMPC (d) liposomes. In this case, the systems were composed of DOPC (dioleoylphosphatidylcholine) liposomes or DMPC (dimyristoylphosphatidylcholine) α-cyclodextrin. The insets represent the method for determining the cyclodextrin/lipid ratios and show the increase in the OD preceding the plateau of the turbidity curves.

Figure 4:
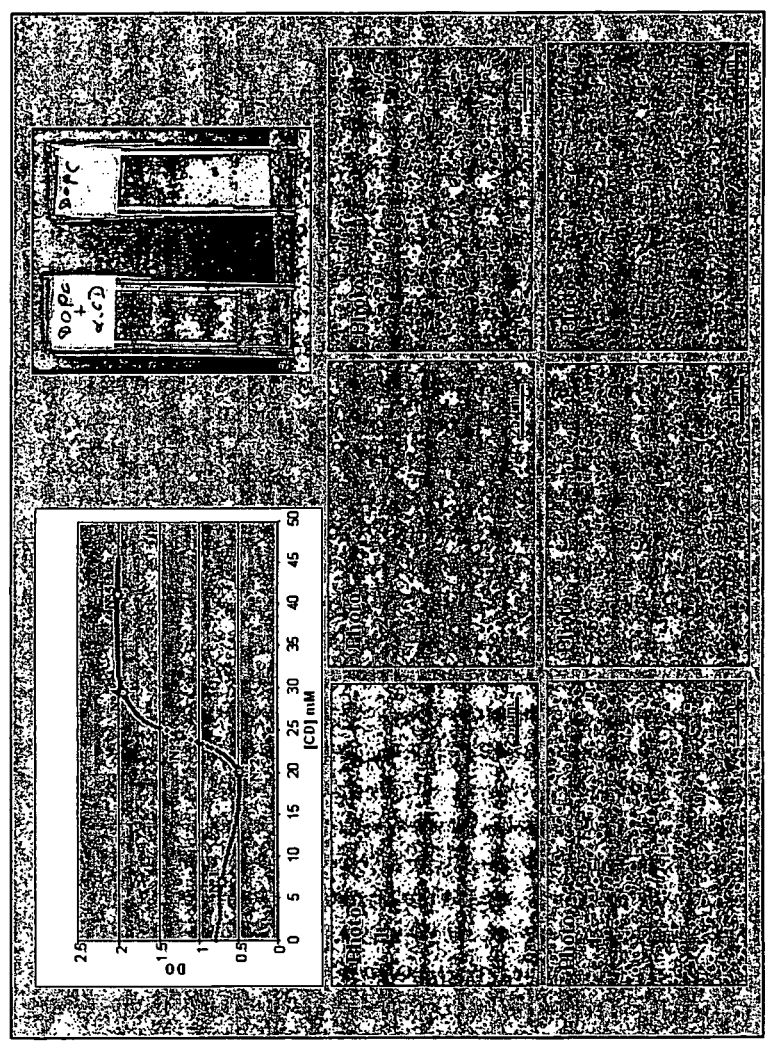

FIG. 4: Illustration of the process of concentrating DOPC liposomes in the presence of α-CD. Investigation carried out by measuring the turbidity (OD at 400 nm) and by using light microscopy (×40). Each point marked on the turbidity curve corresponds to a sample analysed by microscopy. The photograph on the right hand side shows liposomes before the addition of cyclodextrin and, adjacent thereto, the final state of aggregation at the plateau of the turbidity curve. When the OD increases, the liposomes become concentrated and flocculate, which translates in light microscopy as an increase in the concentration of objects in a given volume of the sample. Photo 1 shows the liposomes in the absence of cyclodextrin. They are very diluted and too small to be seen.

Figure 5:
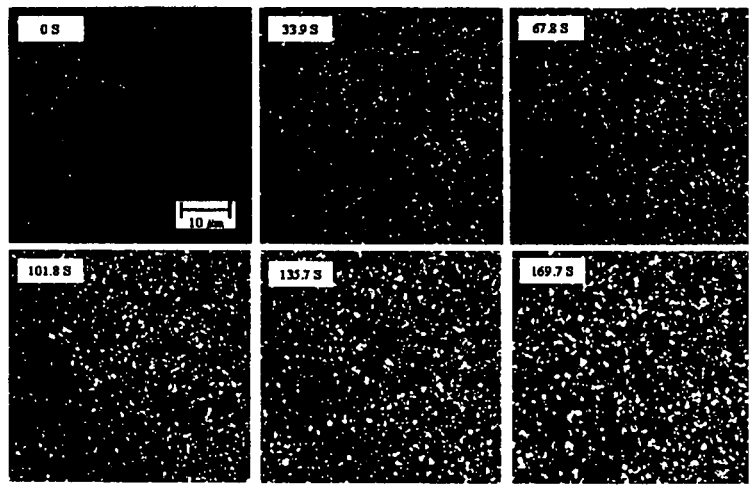

FIG. 5: Confocal microscopy images as a function of time of the fluorescence of DOPC liposomes labelled with Rhod-PE (rhodamine distearoylphosphatidyl ethanolamine) before and during the aggregation of said liposomes after the addition of cyclodextrin.

Figure 6:
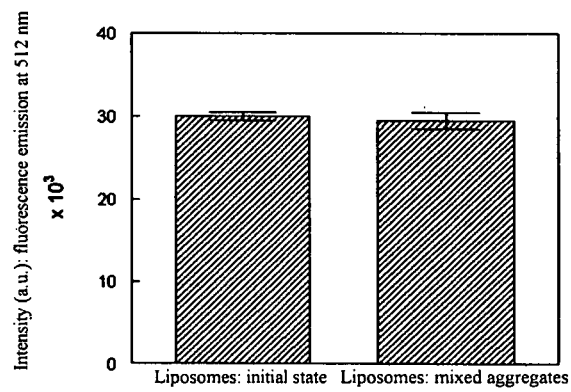

FIG. 6: Fluorescence emission intensity of the calcein contained in DOPC liposomes before and after aggregation. The spectra were recorded after the liposomes were solubilised by an octyl glucoside detergent so as to release the calcein molecules trapped in the liposomes. The aggregated liposomes were separated beforehand from the continuous aqueous medium by means of centrifugation.

FIG. 7: Study of the disintegration of DOPC liposomes, previously aggregated by the addition of cyclodextrin, by means of simple dilution. Light microscopy on a black field (×40).

FIG. 8: Light microscopy images (×40) of liposomes with a diameter of 800 nm and cyclodextrin.

Figure 9:
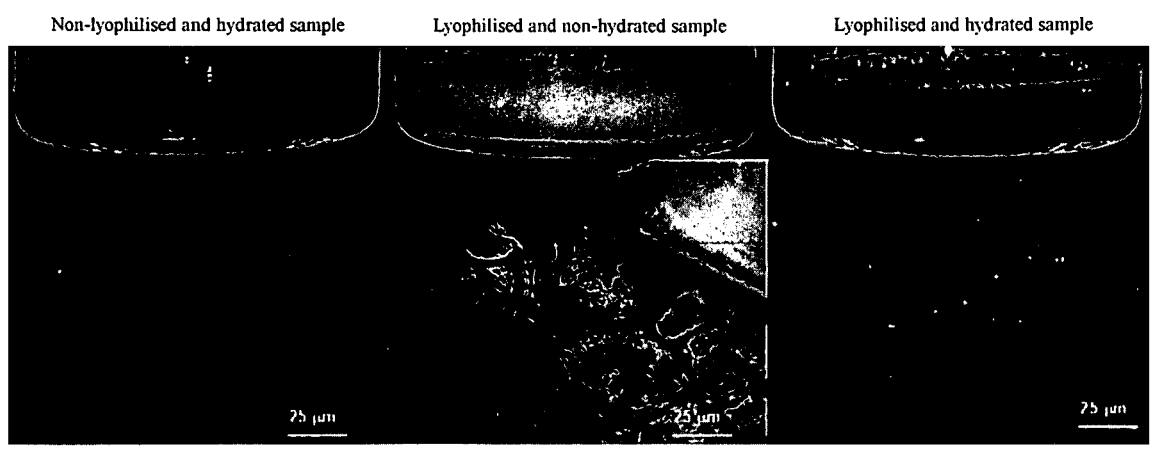

FIG. 9: Light microscopy images (×40) and photographs of corresponding samples; from left to right, liposomes without cyclodextrin, the lyophilisate of mixed liposome/cyclodextrin aggregates, liposomes after the rehydration of the lyophilisate.

Figure 10:

FIG. 10: Scanning electron microscopy images of a lyophilisate of mixed liposome/cyclodextrin aggregates. The cyclodextrin molecules form a matrix shaped as plates with a square cross-section of approximately 2 µm² in size, in which spherical structures, having a diameter of approximately 200 nm and corresponding to the liposomes which form the precursor aggregates, are trapped. The lyophilisation process therefore conserves the structure of the liposomes which form the mixed liposome/cyclodextrin aggregates. The device used was a LEO 9530 (France). The samples were covered by a platinum/palladium deposit before analysis.

FIG. 11: Freeze-fracture electron microscopy images of liposomes obtained after dialysis of DMPC liposome/α-cyclodextrin mixed aggregates obtained by a concentration process (DMPC concentration: 0.4 mM, α-cyclodextrin concentration; 15.6 mM).

Figure 12:
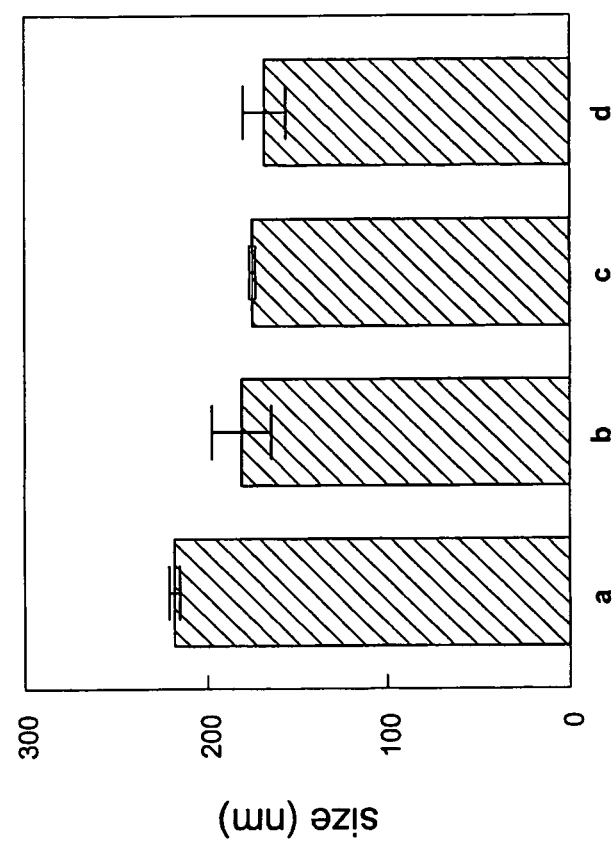

FIG. 12: Average hydrodynamic diameters (in nm) measured by quasielastic light scattering of DOPC or DMPC liposomes before (a, c) and after (b, d) dialysis of the mixed liposome/α-cyclodextrin aggregates obtained by the concentration process. The DOPC phospholipid concentration was 0.3 mM (a, b) and the DMPC phospholipid concentration was 0.4 mM (c, d). The α-cyclodextrin concentration used for the concentration process was 28.4 mM (b) or 15.6 mM (d).

The following examples illustrate the invention without limiting it in any way. The starting products used are known products or products prepared in accordance with known methods.

The percentages are expressed in weight, unless there is an indication to the contrary.

EXAMPLES

Example 1: Formation of Aggregates (Concentrated Liposomes)

The process is applicable to any type of liposome, in particular those composed predominantly of phospholipids, whatever the preparation method and final structure (size, shape, composition) thereof. The process was generally tested on unilamellar liposomes (average diameter: 200 nm) and on oligolamellar liposomes (average diameter: 1 μm).

Step 1: Preparation

In a preferred embodiment of the present invention, the liposomes used were prepared by hydrating a film of phospholipids, followed by sequenced extrusion to size the vesicles. The phospholipid film was obtained by evaporating the solvent in a chloroform solution of phospholipids under a flow of nitrogen. The remaining traces of solvent were removed by lyophilisation under a high vacuum for twelve hours. This film was subsequently hydrated with a predetermined volume of an aqueous phase (RO water, phosphate buffer, PBS buffer, Hepes buffer, Hepes buffer+NaCl) in such a way that the total phospholipid concentration was 10 nM. The dispersion was kept at 25° C. in a water bath and was homogenised by stirring by means of a vortex. The final dispersion was liquid and opalescent. This dispersion was subsequently extruded by being passed successively through Poretics® poly(carbonate) filters (Osmonics, Livermore, USA) with pore diameters of decreasing size (0.8; 0.4 and 2×0.2 μm) by using a laboratory-constructed extruder under nitrogen pressure. After the final extrusion procedure, vesicles which were predominately unilamellar, of homogenous size and stable over time were obtained. The change in size was monitored by quasielastic light scattering (nanosizer from Coulter Electronics LTD).

Step 2: Concentration Process a) Flocculation

The liposomes were brought to the final concentration selected by adding the dispersant aqueous phase. An α-cyclodextrin (α-CD) solution prepared in the same medium was subsequently added in one go. At the end of a period of time of between 1 and 10 minutes, the liposomes flocculated in the form of a dispersion of aggregates with diameters ranging between 800 nm and several microns. FIG. 1 shows the change in turbidity of the sample over the course of time by measuring the optical density (OD). The higher the OD value, the higher the aggregate content. The final plateau indicates that the period of time required for flocculation has come to an end. It was observed that the estimated time for obtaining aggregates decreased as the α-cyclodextrin concentration increased. The cyclodextrin concentration is therefore a parameter governing the rate of liposome aggregation in the dispersion.

b) Sedimentation

The flocculation process was followed by a spontaneous sedimentation process which due to the density of the aggregates resulted in the deposition of mixed liposome-cyclodextrin aggregates (FIG. 2). The duration of this process ranged between several hours and 24 hours depending on the initial liposome and cyclodextrin concentrations.

Example 2: Effect of the Cyclodextrin/Phospholipid Molar Ratio on the Liposome Concentration Process Monitoring the turbidity of the liposome dispersions as a function of the proportions of added cyclodextrin, aqueous phase and liposomes by measuring the optical density (OD) with a UV-Visible spectrophotometer allowed the zone(s) of aggregate formation to be determined precisely and thus the liposome concentration conditions to be characterised.

This example was performed using unilamellar DOPC liposomes with an average diameter of 200 nm which were obtained by extrusion. The DOPC liposomes were placed at different lipid concentrations (from 0.5 to 5 mM) in a quartz cell, which allowed the OD to be recorded continuously. An α-cyclodextrin solution (80 mM) was added gradually. The results obtained (FIG. 3 a, b) show that, in order to achieve the flocculation of liposomes and thus the concentration thereof in the medium, the lower the initial liposome concentration is, the higher the concentration of added α-cyclodextrin should be. The formation of the flocculate is indicated by a rapid increase in the optical density. The proportions of the three components of the mixture have an effect on the formation time and the size of the aggregates obtained.

TABLE 1

Effect of the [α-CD]/[DOPC] ratio on the formation of the flocculate (the size, the appearance on a microscopic scale (X40) and the apparent density thereof (−−) very low, (−) low, (+) average, (++) high, (+++) very high). See also FIG. 4.

| [αCD] mM | [DOPC] mM | [αCD]/[DOPC] ratio | Flocculate density | Size of mixed liposome/cyclodextrin aggregates | Location on the curve | Light microscopy (X40) |
|---|---|---|---|---|---|---|
| 0 | 0.49 | 0 | −− | liposomes only: 0.2 ± 0.017 μm | Point No. 1 | Photo 1 |
| 6.59 | 0.458 | 14.4 | − | 1.9 ± 0.2 μm | Point No. 2 | Photo 2 |
| 19.58 | 0.383 | 51.4 | + | 3 ± 1 μm | Point No. 3 | Photo 3 |
| 23.95 | 0.358 | 66.8 | ++ | 3.5 ± 1.5 μm | Point No. 4 | Photo 4 |
| 28.4 | 0.333 | 85.3 | +++ | 4 ± 2 μm | Point No. 5 | Photo 5 |
| 39.24 | 0.271 | 144.9 | +++ | 4.8 ± 3 μm | Point No. 6 | Photo 6 |

The same experiment was carried out using DMPC dimyristoylphosphatidylcholine liposomes (synthetic lipid with saturated chains). The results are shown in FIG. 3 c, d.

TABLE 2

Example of the effect of the dispersant phase on the formation of aggregates composed of DOPC liposomes (0.064 mM) and an α-CD solution (75.5 mM); (+) low density of aggregates, (++) average density, (+++) high density, (−) no flocculation.

| Aqueous phase | pH | DOPC + aqueous phase | α-CD + aqueous phase | DOPC + aqueous phase + α-CD | Aggregate size | Microscopic appearance |
|---|---|---|---|---|---|---|
| Osmosis water | 5.5-6 | − | − | + | 2.5 μm | 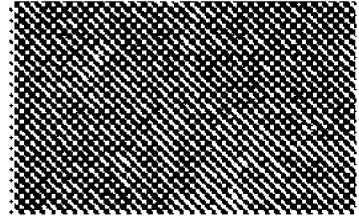 |
| Phosphate buffer | 7.3 | − | − | +++ | 5-15 μm |  |
| PBS buffer | 7.2 | − | − | ++ | 1.5-6.5 μm |  |
| Hepes buffer | 7.4 | − | − | + | 1.5 μm | 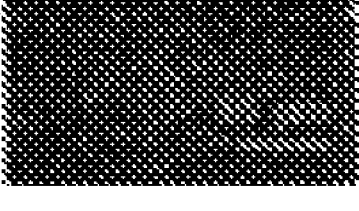 |

TABLE 2-continued

Example of the effect of the dispersant phase on the formation of aggregates composed of
DOPC liposomes (0.064 mM) and an α-CD solution (75.5 mM); (+) low density of aggregates,
(++) average density, (+++) high density, (−) no flocculation.

| Aqueous phase | pH | DOPC + aqueous phase | α-CD + aqueous phase | DOPC + aqueous phase + α-CD | Aggregate size | Microscopic appearance |
|---|---|---|---|---|---|---|
| Hepes buffer + NaCl | 7.4 | − | − | ++ | 4 µm |  |

Example 3: Concentration of Liposomes Containing an Exogenous Substance

Two model substances were tested.

a) Example of a Lipophilic Molecule: Rhodamine Distearoylphosphatidyl Ethanolamine (Rhod-PE)

Rhod-PE is a phospholipid bearing a fluorescent group (rhodamine). The experiment was carried out by using fluorescence confocal microscopy. The results show that the flocculation process, caused by α-cyclodextrin, of liposomes filled with Rhod-PE (prepared in accordance with the method described in Example 1) does not change the fluorescence of the liposomes. Fluorescence confocal microscopy clearly shows aggregates of fluorescent liposomes (FIG. 5).

b) Example of a Hydrophilic Molecule: Calcein

Calcein is a fluorescent molecule which has a low molar mass and is soluble in water. No trace of calcein which was encapsulated beforehand in the DOPC liposomes was detected in the supernatant by fluorescence spectrophotometry after the spontaneous liposome sedimentation caused by the addition of cyclodextrin. Furthermore, the amount of calcein contained in the liposomes was retained in the aggregates (FIG. 6). It therefore appears that the impermeability of the liposome membrane is not modified by the cyclodextrin molecules.

Example 4: Reversibility of the Process by a Simple Dilution Procedure

The first step of the process was carried out as described in the preceding paragraph. A concentrate of liposomes and cyclodextrins was obtained in the form of a white precipitate. A volume of an aqueous phase was subsequently added (final dilution×100 by volume) and the change in the system was monitored by means of light microscopy (FIG. 7). The liposomes disintegrated within several minutes as the aqueous phase progressed further into the liposome concentrate until the liposomes were dispersed in the medium without there being any interaction between said liposomes; these liposomes appear as small isolated dots when viewed by means of microscopy on a black field.

The same experiment was reproduced for liposomes containing Rhod-PE. The change in the liposome concentrate was monitored by means of fluorescence confocal microscopy (λexc=488 nm, λem=543 nm) at 25° C. It can clearly be seen that the liposomes remain fluorescent and are redispersed in the medium after dilution.

The same experiment was also carried out with liposomes containing calcein in the internal aqueous volume thereof. The emission spectra for calcein recorded for the liposome preparations before aggregation and after aggregation/redispersion are superposable (form and intensity). In addition, the average liposome diameter measured by quasielastic light scattering was retained.

Example 5: Characterisation of the Concentrated Liposome-Cyclodextrin Mixture (Mixed Aggregates)

Macroscopic Appearance

The aggregates formed by α-cyclodextrin and liposomes formed a suspension which was deposited over time. The sedimentation process was complete after a period of time ranging between several hours and 24 hours. This sedimentation process enabled the liposomes to be concentrated in a very low volume. The system was able to be redispersed by simply being stirred, without the aggregates disintegrating. The aggregates formed were stable over time at room temperature. They were light in colour and their size varied between 1 and 20 µm depending on the liposome and cyclodextrin concentrations used. The dimensions of said aggregates may change upon being subjected to a light shear force.

Microscopic Appearance

The microscopic study (×20) of the system of liposomes with an initial diameter of 800 nm showed that the presence of cyclodextrin results in the spontaneous aggregation of liposomes. Said liposomes thus form clusters of intact liposomes (FIG. 8).

Suitability for Lyophilisation

Light microscopy showed that the "clusters" of liposomes (DMPC (200 nm), α-cyclodextrin) formed in this way can undergo lyophilisation without this process altering the characteristics of the individual liposomes. Rehydrating the lyophilisate enables the liposomes to be returned to their initial state without modifying the appearance thereof (FIG. 9).

The sample produced by rehydrating the lyophilisate was diluted so as to disintegrate the liposome-cyclodextrin aggregates. Quasielastic light scattering measurements showed that the initial diameter of the liposomes before concentration (200 nm) was also retained after lyophilisation/rehydration. The concentration process developed is therefore an excellent tool for preparing lyophilised liposomes without modifying the initial characteristics thereof.

Experiments were carried out on mixed liposome/cyclodextrin samples after aggregation and after lyophilisation by using scanning electron microscopy. The pictures clearly show liposomes with dimensions very similar to those of the liposomes in the hydrated aggregates which are trapped in a cyclodextrin matrix (FIG. 10).

Example 6: Dispersion of Liposomes by Means of Dialysis of the Mixed Liposome/α-Cyclodextrin Aggregates The first step of the process was carried out as described in Example 1. A liposome and α-cyclodextrin concentrate was obtained in the form of a white precipitate. For initial phospholipid concentrations of 0.5 mM and initial concentrations of α-cyclodextrin of between 15 and 30 mM, 2 ml of the preparation containing the mixed liposome/α-cyclodextrin aggregates was typically placed in a dialysis chamber provided with a Spectrapore membrane (cut-off 12,000 Da) which allowed the cyclodextrin molecules but not the liposomes to pass through. The chamber was subsequently placed in a 1-liter beaker containing 800 ml of the aqueous medium used to produce the initial liposomes. The equipment and the contents, i.e. the chamber and the aqueous medium, were stirred gently using a magnetic stirring bar at 25° C. The dialysis bath was replaced twice during every 24 hour period. At the end of the dialysis process (2×800 ml per 24 hours over 3 days), a dispersion of individual liposomes (see FIG. 11) in a volume equal to that of the initial sample (2 ml) was obtained in the dialysis chamber. The liposome concentration after dialysis was that of the mixed aggregates obtained by the concentration process. Eliminating the α-cyclodextrin molecules thus caused the liposomes to disintegrate, and the average diameter of these liposomes, measured by means of quasielastic light scattering, was very close to that of the initial liposomes (see FIG. 12). Like Example 4, this also shows that the concentration process is reversible. Using dialysis advantageously enables the initial concentration of the initial mixed liposome/α-cyclodextrin aggregates to be retained, since no dilution takes place in the dialysis chamber. Furthermore, the use of dialysis ensures the absence of free α-cyclodextrin molecules in the aqueous medium in equilibrium with the redispersed liposomes, but this does not rule out the possibility that a small amount of α-cyclodextrin molecules ultimately remain adsorbed to the surface of the liposomes, forming new nanoparticulate hybrid systems described as vesicle structures delimited by a bilayer of phospholipids which in turn is covered by one or more layers of α-cyclodextrin molecules.

The same experiment may be reproduced by using the concentrate of mixed aggregates which are obtained by the concentration process and are then separated by decanting the excess aqueous medium. In this respect, dialysis advantageously enables a dispersion of individual liposomes to be produced which is at least 4 times more concentrated than the liposomes before the formation of mixed liposome/α-cyclodextrin aggregates.

The same experiment may be reproduced by using a lyophilisate of the mixed liposome/α-cyclodextrin aggregates as described in example 5 and by subsequently rehydrating this lyophilisate with an amount of aqueous medium which is adjusted to the final concentration of individual liposomes which it is desired to obtain after the dialysis step.

The invention claimed is:

1. A process for preparing liposomes, said process comprising the following steps:
encapsulating at least one ingredient in liposomes comprising phospholipids, said liposomes being dispersed in an aqueous medium, to form liposomes encapsulating said at least one ingredient in the aqueous medium;
bringing said liposomes encapsulating said at least one ingredient, which are dispersed in the aqueous medium, into contact with natural α-cyclodextrins optionally modified with hydrophilic chemical groups so that the aqueous medium has a molar concentration of said α-cyclodextrins and a molar concentration of said liposomes, the molar concentration of said α-cyclodextrins being equal to or greater than the molar concentration of said liposomes;
forming liposomes-cyclodextrins aggregates, the formed liposomes-cyclodextrins aggregates flocculating and sedimenting in the aqueous medium to form a deposit, said deposit of liposomes-cyclodextrins aggregates constituting a concentrate of liposomes and encapsulating said at least one ingredient;
recovering said liposomes-cyclodextrins aggregates encapsulating said at least one ingredient; and
disintegrating the liposomes-cyclodextrins aggregates encapsulating said at least one ingredient to recover individual liposomes encapsulating said at least one ingredient.

2. The process as claimed in claim 1, wherein all or part of the cyclodextrins of said liposomes-cyclodextrins aggregates contain said at least one ingredient, and said at least one ingredient is a cosmetic, therapeutic or diagnostic active ingredient.

3. The process as claimed in claim 1, wherein the liposomes consist of phospholipids.

4. The process as claimed in claim 3, wherein the phospholipids are phosphatidylcholines.

5. The process as claimed in claim 1, wherein the aqueous medium is buffered to a pH of between 6 and 8.

6. The process as claimed in claim 1, wherein the aqueous medium contains a monovalent salt.

7. The process as claimed in claim 1, wherein all or part of the liposomes are biological cells.

8. A process for preparing liposomes-cyclodextrins aggregates, said process comprising the following steps:
bringing liposomes comprising phospholipids, which are dispersed in an aqueous medium, into contact with natural α-cyclodextrins optionally modified by hydrophilic chemical groups so that the aqueous medium has a molar concentration of said α-cyclodextrins and a molar concentration of said liposomes, the molar concentration of said α-cyclodextrins being equal to or greater than the molar concentration of said liposomes;
forming liposomes-cyclodextrins aggregates, the formed liposomes-cyclodextrins aggregates flocculating and sedimenting in the aqueous medium to form a deposit;
lyophilizing said deposit of liposomes-cyclodextrins aggregates to obtain lyophilized liposomes-cyclodextrins aggregates;
rehydrating said lyophilized liposomes-cyclodextrins aggregates to recover liposomes-cyclodextrins aggregates; and
dialysing the liposomes-cyclodextrins aggregates to disintegrate the liposomes-cyclodextrins aggregates to recover individual liposomes.

9. A method of encapsulating exogenous substances comprising forming liposomes-cyclodextrins aggregates as defined in claim 1, wherein all or part of the liposomes contain as an exogenous substance said at least one ingredient, wherein the exogenous substance is selected from the group consisting of a cosmetic active agent, a therapeutic active agent and a diagnostic active agent for the preparation of cosmetic pharmaceutical or diagnostic compositions.

10. A process of forming liposomes, said process comprising the following steps:
bringing liposomes comprising phospholipids, which are dispersed in an aqueous medium, into contact with natural α-cyclodextrins optionally modified by hydrophilic chemical groups so that the aqueous medium has a molar concentration of said liposomes of 0.05 mM to 5 mM and a molar concentration of said α-cyclodextrins that is equal to or greater than the molar concentration of said liposomes,
forming liposomes-cyclodextrins aggregates, said liposomes-cyclodextrins aggregates flocculating and sedimenting in the aqueous medium to form a deposit; and
recovering and optionally concentrating said liposomes-cyclodextrins aggregates; and
recovering individual liposomes from said optionally concentrated liposomes-cyclodextrins aggregates.

11. A process of forming liposomes, said process comprising the following steps:
bringing liposomes comprising phospholipids, which are dispersed in an aqueous medium, into contact with natural α-cyclodextrins optionally modified by hydrophilic chemical groups;
forming liposomes-cyclodextrins aggregates in the aqueous medium;
flocculating and sedimenting said liposomes-cyclodextrins aggregates in the aqueous medium;
forming liposomes-cyclodextrins aggregates, optionally concentrating said liposomes-cyclodextrins aggregates; and
dialyzing said liposomes-cyclodextrins aggregates thereby disintegrating the liposomes-cyclodextrins aggregates to recover individual liposomes.

12. A process of reversible aggregation of liposomes, said process comprising the following steps:
dispersing in an aqueous medium liposomes comprising phospholipids;
bringing said liposomes comprising phospholipids, which are dispersed in an aqueous medium, into contact with natural α-cyclodextrins optionally modified by hydrophilic chemical groups;
aggregating the liposomes by forming liposomes-cyclodextrins aggregates in the aqueous medium;
concentrating said liposomes-cyclodextrins aggregates in the aqueous medium without further processing said liposomes-cyclodextrins aggregates with ultracentrifugation or ultrafiltration steps; and
disintegrating the liposomes-cyclodextrins aggregates through addition of an aqueous medium to recover individual liposomes.

13. The process as claimed in claim 1, wherein the phospholipids are selected from the group consisting of: phosphatidylcholine (PC) egg phosphatidylcholine (Egg-PC), dimyristoylphosphatidylcholine (DMPC), dioleoylphosphatidylcholine (DOPC), dilauroylphosphatidylcholine (DLPC), distearoylphosphatidylcholine (DSPC), diarachidoylphosphatidylcholine (DAPC), dilinoleoylphosphatidylcholine (DLPC), and mixtures thereof.

14. The process as claimed in claim 1, wherein the molar concentration of α-cyclodextrins is at least twice but no more than 1,500 times the molar concentration of liposomes in the aqueous medium.

15. The process as claimed in claim 1, wherein all or part of the liposomes contain said at least one ingredient as an exogenous substance.

16. The process as claimed in claim 1, further comprising lyophilizing said recovered liposomes-cyclodextrins aggregates encapsulating said at least one ingredient prior to disintegrating.

17. The process as claimed in claim 16, wherein said liposomes-cyclodextrins aggregates encapsulating said at least one ingredient are disintegrated by rehydrating the lyophilized liposomes-cyclodextrins aggregates encapsulating said at least one ingredient, optionally followed by a dialysis step, to recover said individual liposomes encapsulating said at least one ingredient.

18. The process as claimed in claim 1, wherein said liposomes-cyclodextrins aggregates encapsulating said at least one ingredient are recovered by filtration or centrifuging of said aqueous medium containing said deposit of liposomes-cyclodextrins aggregates encapsulating said at least one ingredient.

* * * * *